(12) United States Patent　　(10) Patent No.: US 8,976,931 B2
Lalena　　(45) Date of Patent: Mar. 10, 2015

(54) MOBILE RADIOGRAPHY IMAGING APPARATUS USING PRIOR RELATED IMAGES BEFORE CURRENT IMAGE EXPOSURE AND METHODS FOR SAME

(75) Inventor: Michael C. Lalena, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 539 days.

(21) Appl. No.: 13/085,809

(22) Filed: Apr. 13, 2011

(65) Prior Publication Data

US 2011/0311026 A1　Dec. 22, 2011

Related U.S. Application Data

(60) Provisional application No. 61/323,494, filed on Apr. 13, 2010.

(51) Int. Cl.
*A61B 6/00* (2006.01)
*G06F 19/00* (2011.01)

(52) U.S. Cl.
CPC ............... *A61B 6/4405* (2013.01); *A61B 6/465* (2013.01); *A61B 6/542* (2013.01); *A61B 6/545* (2013.01); *A61B 6/563* (2013.01); *G06F 19/3406* (2013.01)
USPC ....................................................... 378/98.5

(58) Field of Classification Search
USPC ................................. 378/98.5, 196, 197, 198
See application file for complete search history.

(56) References Cited

U.S. PATENT DOCUMENTS

| | | | |
|---|---|---|---|
| 3,974,385 A * | 8/1976 | Grim | 378/97 |
| 5,844,961 A | 12/1998 | McEvoy et al. | |
| 6,901,277 B2 | 5/2005 | Kaufman et al. | |
| 7,130,457 B2 | 10/2006 | Kaufman et al. | |
| 7,611,282 B2 | 11/2009 | Koren et al. | |
| 2004/0240624 A1* | 12/2004 | Shiibashi et al. | 378/197 |
| 2005/0192495 A1 | 9/2005 | Makram-Ebeid et al. | |
| 2006/0195484 A1 | 8/2006 | Mahesh et al. | |
| 2007/0076929 A1 | 4/2007 | Gentles et al. | |
| 2007/0112596 A1* | 5/2007 | Exelmans | 705/2 |
| 2007/0116182 A1* | 5/2007 | Koren | 378/198 |
| 2008/0077001 A1 | 3/2008 | Ruscio et al. | |
| 2008/0152086 A1 | 6/2008 | Hall et al. | |
| 2009/0147909 A1* | 6/2009 | Yoda et al. | 378/4 |
| 2010/0128991 A1 | 5/2010 | Weese et al. | |
| 2010/0131292 A1 | 5/2010 | Hawkins et al. | |

FOREIGN PATENT DOCUMENTS

| | | |
|---|---|---|
| WO | WO 2007/078684 | 7/2007 |
| WO | WO 2007/139638 | 12/2007 |
| WO | WO 2010/029470 | 3/2010 |

* cited by examiner

*Primary Examiner* — Glen Kao

(57) ABSTRACT

A mobile radiography apparatus has a moveable (e.g., wheeled) transport frame and an adjustable column mounted at the frame. A boom apparatus supported by the adjustable column can support an x-ray source. A display at the mobile radiography apparatus is configured to provide an examination procedure for a patient, the examination procedure to include a visual indication that at least one related prior image exists for the examination procedure.

18 Claims, 14 Drawing Sheets

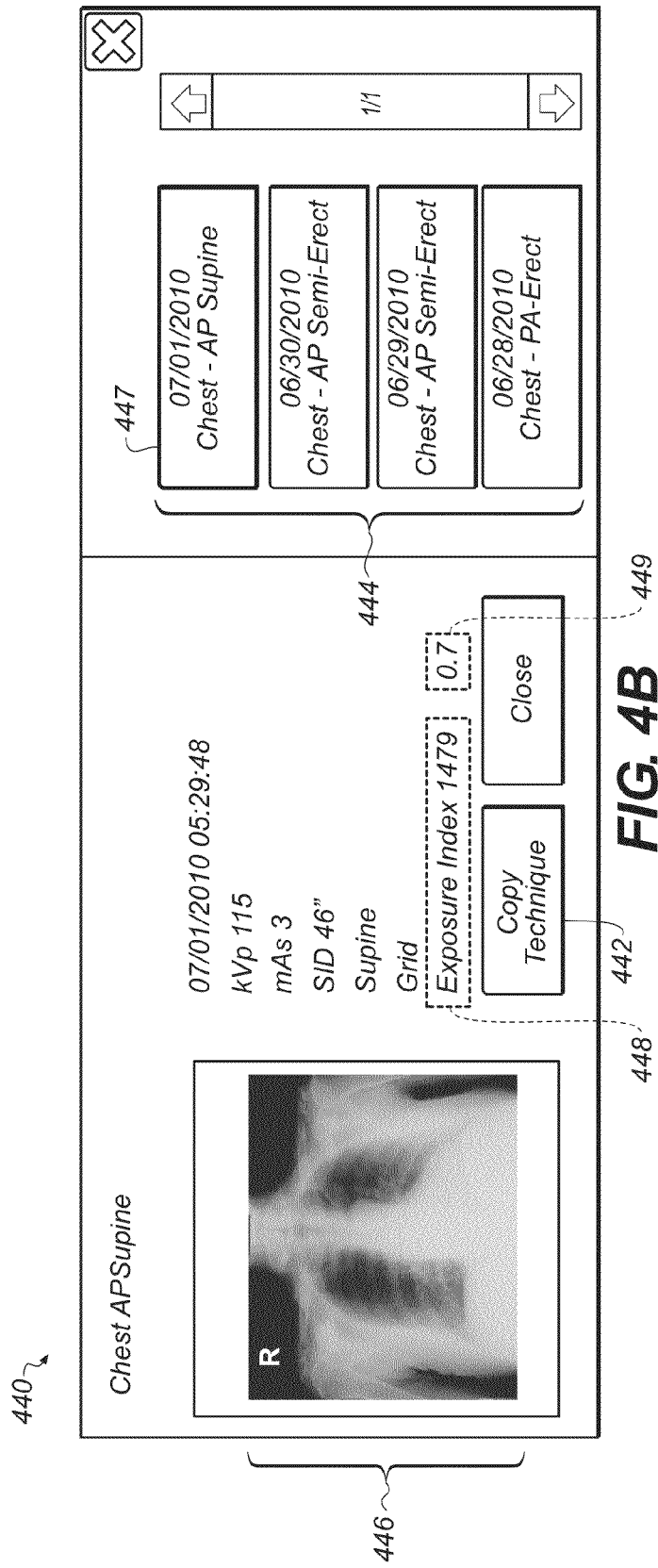

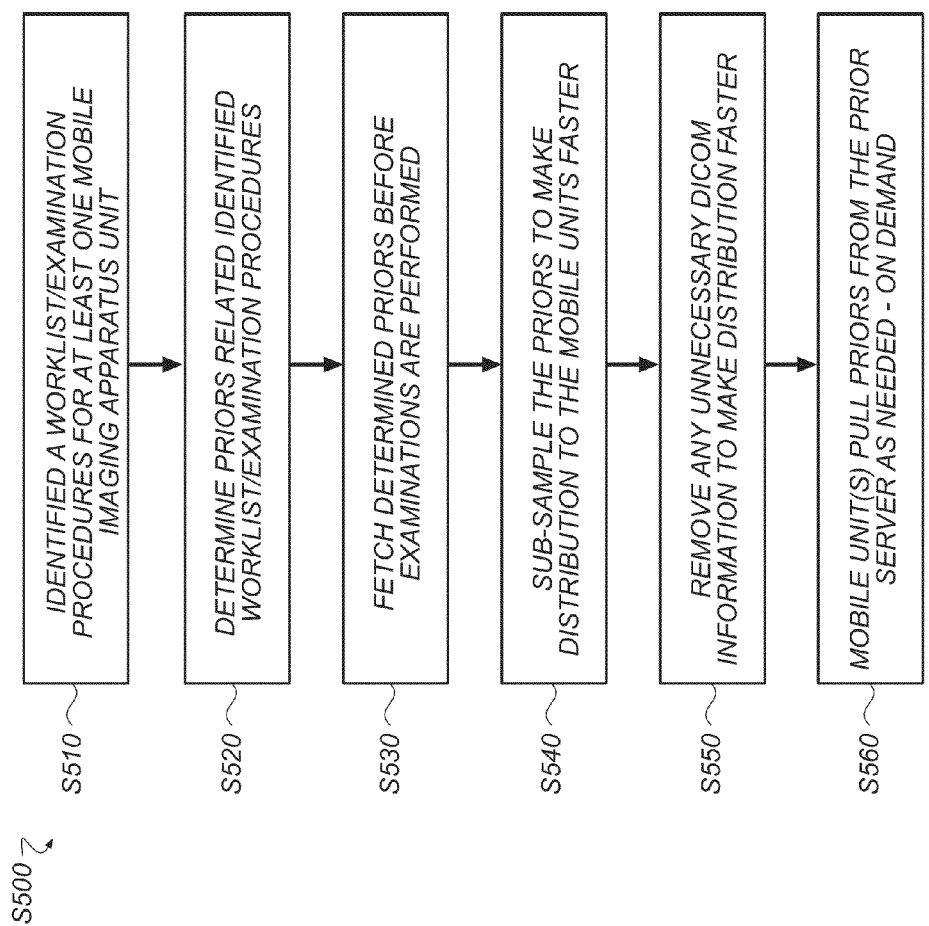

| WORK LIST | | | |
|---|---|---|---|
| PATIENT NAME | EXAM TIME | PROCEDURE NAME | PATIENT ROOM |
| PETERSON, GEOFF | 2/9/2011 11:10 | SKULL - 4 VIEWS | Rm 204 |
| PETERSON, GEOFF | 2/9/2011 12:51 | ORBITS - 5 VIEWS | Rm 204 |
| PETERSON, GEOFF | 2/9/2011 11:10 | ELBOW - 4 VIEWS | Rm 204 |
| PETERSON, GEOFF | 2/9/2011 12:51 | ADULT CHEST - 6 VIEWS | Rm 204 |
| PETERSON, GEOFF | 2/9/2011 11:10 | ELBOW - 4 VIEWS | Rm 204 |
| PETERSON, GEOFF | 2/9/2011 12:51 | ADULT CHEST - 6 VIEWS | Rm 204 |

NEW EXAM REQUESTED

EXAM TIME: 4/11/2010 11:25:01 AM

LOCATION: Rm 816

PATIENT NAME: MARK BAILEY

EXAM: PORTABLE HIP

ROUTINE

*FIG. 7*

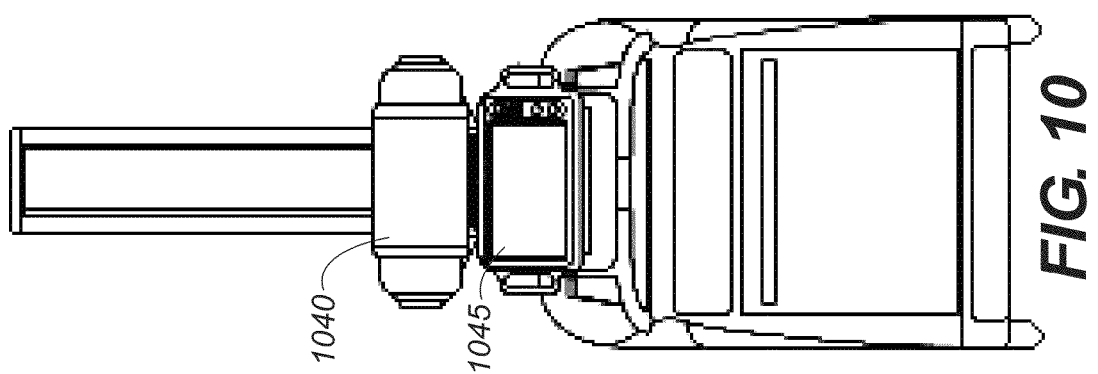

MOBILE RADIOGRAPHY IMAGING APPARATUS USING PRIOR RELATED IMAGES BEFORE CURRENT IMAGE EXPOSURE AND METHODS FOR SAME

CROSS REFERENCE TO RELATED APPLICATIONS

Priority is claimed from commonly assigned, U.S. provisional patent application Ser. Nos. 61/323,494, filed Apr. 13, 2010, entitled "DISPLAYING PRIOR IMAGES AND TECHNIQUES", in the name of Michael C. Lalena, the disclosure of which is incorporated by reference.

FIELD OF THE INVENTION

The invention relates generally to the field of medical imaging, and in particular to radiographic imaging and portable radiographic imaging apparatus. More specifically, the invention relates to methods and apparatus to provide related prior radiographic images (e.g., to a technician) before and to aid in obtaining a next radiographic image.

BACKGROUND

Stationary radiographic imaging equipment are employed in medical facilities (e.g., in a radiological department) to capture (e.g., digital) medical x-ray images on x-ray detector. Mobile carts are employed in medical facilities to move medical equipment between locations. One type of mobile cart includes an x-ray source used to capture (e.g., digital) x-ray images on x-ray detector. Medical x-ray images can be captured using various techniques such as computed radiography (CR) and digital radiography (DR) to obtain medical images. Refer also to U.S. Pat. No. 7,611,282 (Koren) and WO 2007/139638 (Jadrich), and WO 2007/078684 (Dhurjaty), and U.S. Pat. No. 5,844,961 (McEvoy).

Mobile x-ray apparatus are of particular value in intensive care unit (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

However, there is a need for improvements in the consistency and/or quality of medical x-ray images, particularly when obtained by a mobile x-ray apparatus design to operate with a non-integrated x-ray detector.

SUMMARY OF THE INVENTION

An aspect of this application is to advance the art of medical radiography.

Another aspect of this application to address in whole or in part, at least the foregoing and other deficiencies in the related art.

It is another aspect of this application to provide in whole or in part, at least the advantages described herein.

An aspect of this application to is to address the need for presenting and/or managing prior images in a usable format for use at a radiographic imaging apparatus to obtain an original or primary image.

Another aspect of the application is to provide methods and/or apparatus by which mobile radiography imaging apparatus can be modified to display prior x-ray images (e.g., to a technician) with technique information for a currently scheduled x-ray examination.

Another aspect of the application is to provide methods and/or apparatus by which radiography imaging apparatus can sort a list of related prior x-ray images for a currently scheduled x-ray examination (e.g., for use by a technician).

Another aspect of the application is to provide methods and/or apparatus by which radiography imaging apparatus can copy technique information from a selected prior x-ray image to a currently scheduled x-ray examination (e.g., for use by a technician).

Another aspect of the application is to provide methods and/or apparatus by which radiography imaging apparatus can request and/or receive related prior x-ray images for a patient/technician worklist on demand, responsive to intermittent request, or as scheduled.

Another aspect of the application is to provide embodiments of prior image servers and methods thereof to selectively provide related prior medical images.

In accordance with one embodiment, the present invention can provide a mobile radiography apparatus that can include claim 1.

In accordance with one embodiment, the present invention can provide a method that can include claim 11.

In accordance with one embodiment, the present invention can provide a mobile radiography apparatus that can include claim 17.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 4B is a diagram that shows an exemplary prior image selection screen including an embodiment of a sorted prior images list according to the application.

FIG. 5 is a flow chart that shows an embodiment of a method for prior image acquisition according to the application.

FIGS. 6A-9 are diagrams that illustrate exemplary non-limiting representative functions illustrated on an embodiment of a display of a mobile x-ray imaging apparatus according to the application.

FIG. 10 is a diagram that shows an exemplary embodiment of a display/monitor as a second display mounted to a boom assembly of a mobile radiography unit according to the application.

DESCRIPTION OF EXEMPLARY EMBODIMENTS

Figure 1:
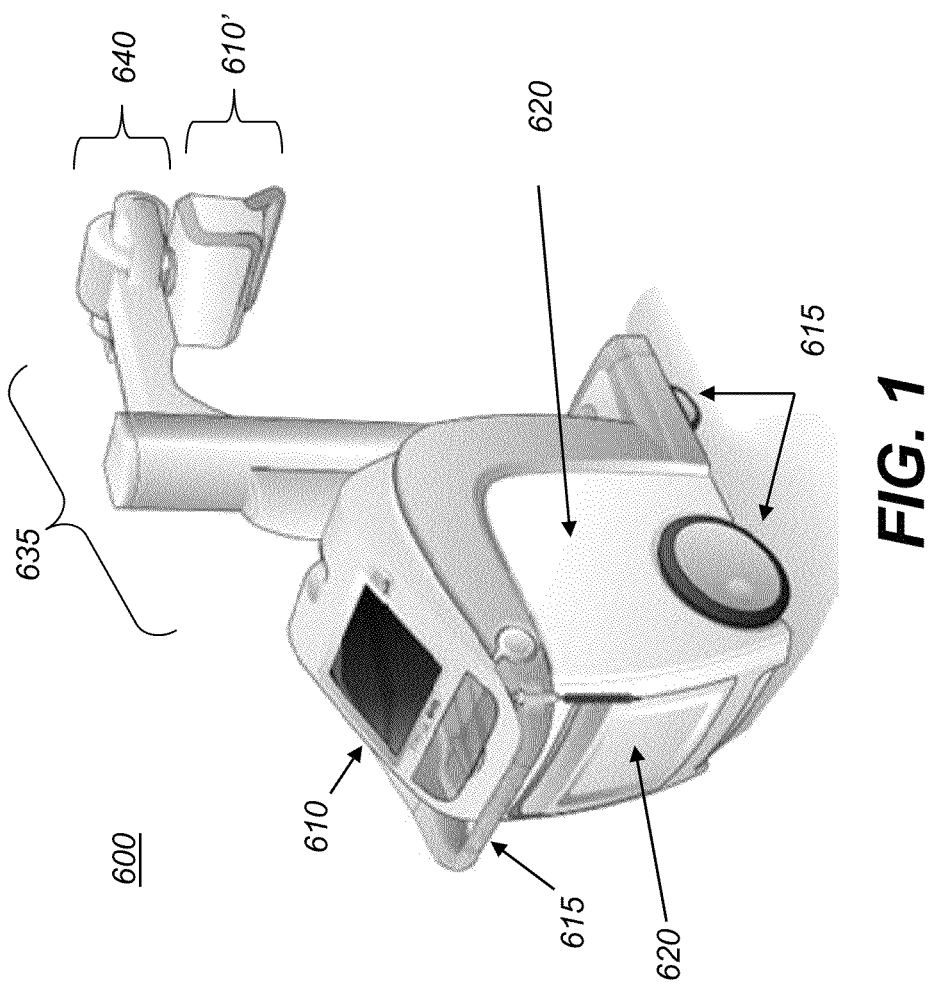
FIG. 1 is a diagram that shows a perspective view of a mobile radiography unit according to one embodiment of the application.

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

FIG. 1 is a diagram that shows a perspective view of a mobile radiography unit capable of prior images display according to an embodiment of the application. The exemplary mobile x-ray or radiographic apparatus of FIG. 1 can be employed for computed radiography (CR) and/or digital radiography (DR). As shown in FIG. 1, a mobile radiography apparatus 600 can include a moveable transport frame 620 that includes a first display 610 and an optional second display 610' for display relevant information such as obtained images and related data. As shown in FIG. 1, the second display 610' can be pivotable mounted at the x-ray source 640 to be viewable/touchable from a 360 degree area around the tube head.

The displays 610, 610' can implement or control (e.g., touch screens) functions such as generating, storing, transmitting, modifying, and printing of an obtained image(s) and can include an integral or separate control panel (not shown) to assist in implementing functions such as generating, storing, transmitting, modifying, and printing of an obtained image(s).

For mobility, the mobile radiographic apparatus 600 has one or more wheels 615 and one or more handle grips 625, typically provided at waist-, arm-, or hand-level, that help to guide the mobile radiography apparatus 600 to its intended location. A self-contained battery pack (e.g., rechargeable) typically provides source power, which can reduce or eliminate the need for operation near a power outlet. Further, the self-contained battery pack can provide for motorized transport.

For storage, the mobile radiography apparatus 600 can include an area/holder for holding/storing one or more digital detectors or computed radiography cassettes. The area/holder can be storage area 630 (e.g., disposed on the frame 620) configured to removably retain at least one digital radiography (DR) detector. The storage area 630 can be configured to hold one or more detectors and can also be configured to hold one size or multiple sizes of detectors.

Mounted to frame 620 is a support column 635 that supports an x-ray source 640, also called an x-ray tube, tube head, or generator that can be mounted to the support column 635. In the embodiment shown in FIG. 1, the support column 635 can include a second section that extends outward a fixed/variable distance from a first section where the second section is configured to ride vertically up and down the first section to the desired height for obtaining the image. In another embodiment, the tube head or x-ray source 640 can be rotatably coupled to the support column 635. In another exemplary embodiment, an articulated member of the support column 635 that bends at a joint mechanism can allow movement of the x-ray source 640 over a range of vertical and horizontal positions. Height settings for the x-ray source 640 can range from low height for imaging feet and lower extremities to shoulder height and above for imaging the upper body portions of patients in various positions.

Figure 2:
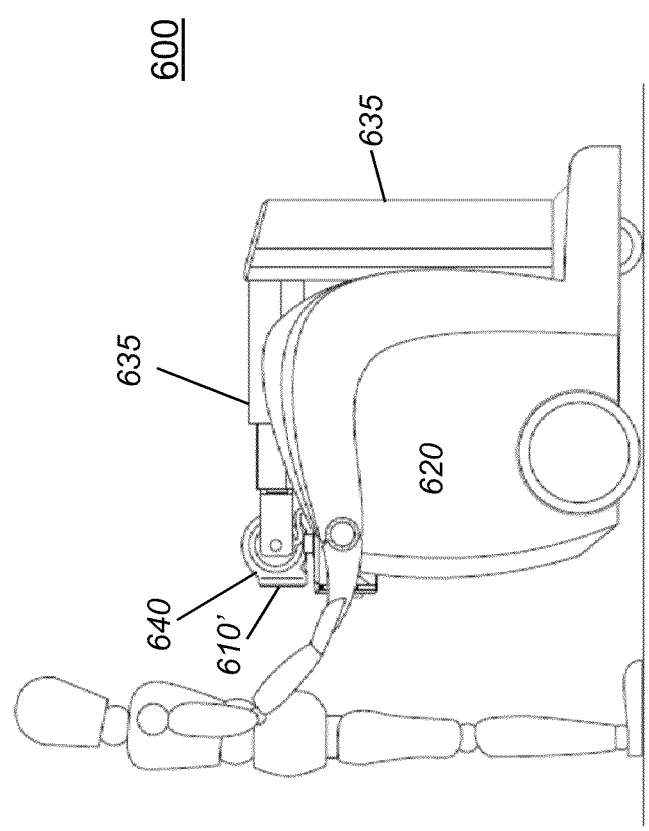
FIG. 2 is a diagram that shows a perspective view of a mobile radiography unit of FIG. 1 positioned for travel.

As shown in FIG. 2, for ease during transport of the mobile radiography apparatus 600, the support member 635 and x-ray source 640 can be arranged close to frame 620. As shown in FIG. 2, the second display 610' can be moved to a viewable position (e.g., operable) during transport of the mobile radiography apparatus 600. In one embodiment, the first display 610 can be disabled during transport. When the mobile radiography apparatus 600 is to be used, the support member 635 and x-ray source 640 can be extended from the frame 620 for proper positioning (e.g., by the operator, a user, or x-ray technician) and the second display 610' moved to viewable position as shown in FIG. 1.

According to exemplary embodiments of the application, the first display 610 and the second display 610' can provide information such as but not limited to: (i) general information such as date, time, environment conditions, and the like; (ii) unit information such as model serial number, operating instructions, warning information, and the like; (iii) patient data, such as patient name, room number, age, blood type, and the like; (iv) indicators such as but not limited to cart power/battery indicators, detector status (e.g., on/off), wireless signal strength/connectivity, grid alignment aides, cart diagnostics and/or (v) imaging/procedure information, such as the exam type, exposure information, and the like.

According to embodiments of the application, the first display 610 and the second display 610' can provide capabilities/functionality to the mobile radiography apparatus 600 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm that the correct patient); (iv) display and/or change a Patient Worklist, such as a list of exams to perform and allow the user to select an exam (In one embodiment, such a patient worklist can be automatically updated (e.g., synchronized to a master/hospital/doctor worklist) using a wired or wireless network/connection. In one embodiment, the mobile radiography apparatus 600 can highlight/indicate new exams (e.g., on the second display 610') upon receipt of the scheduled examination); (v) display generator/source current values and controls to change those values, such as: kVp, mA, mAs, Time, ECF, focal spot, collimator, filter, AEC, grid; (vi) display detector selection and allow the technician to select/activate a different detector; (vii) display recently acquired images and allow editing of those images, exemplary acquired (e.g., recently) or previous images can be displayed full size, partial size or with corresponding image information; (viii) display previously acquired images (e.g., related prior images of a patient) and allow editing of those images; or (ix) display a video of what is in front of the mobile radiography apparatus 600 during transport, e.g., using a video camera located on the other side (e.g., front side of a mobile x-ray imaging apparatus 600).

In the context of the present disclosure, an original or primary image of a subject that is acquired by a system of the present application can include raw image data or may be image data that is automatically pre-processed by the x-ray system itself (so that the raw data is not directly available to users of the system). This can be termed the "primary", "original", or "acquired" image of the subject and can include image data from scanned film, from a computed radiography (CR) imaging system, or from a digital radiography (DR) system, for example.

In the context of the present disclosure, a "prior image" is an image for a patient that was acquired during a previous visit, and preferably, the prior image can be relevant (e.g., same body part) to a current examination to be performed, which will result in a primary image. The capability to view prior images before a current examination to be performed (e.g., for the same patient) including information about imaging techniques used in the prior images can help the technician to obtain a high quality image for the current examination. In one embodiment, a "copy technique" operator action can import specific exposure settings from a selected (e.g., desirable, ideal) prior image among a plurality of prior images for the technician. Prior images can also be related to an identifiable condition or an area of interest in the object to be imaged. Embodiments of systems and/or methods for management and display of prior images can provide a controllable association between prior images and can provide tools for management of that association.

Conventional solutions for image storage and retrieval and for association of multiple images obtained for the same patient employ the PACS (Picture Archiving and Communication System) and various conventional database tools. Thus, as described herein, the PACS is an image store accessible to a radiographic imaging system or an agent thereof to retrieve images therefrom. In one embodiment, the PACS can implement the Digital Imaging and Communications in Medicine (DICOM) data interchange standard.

Figure 3:
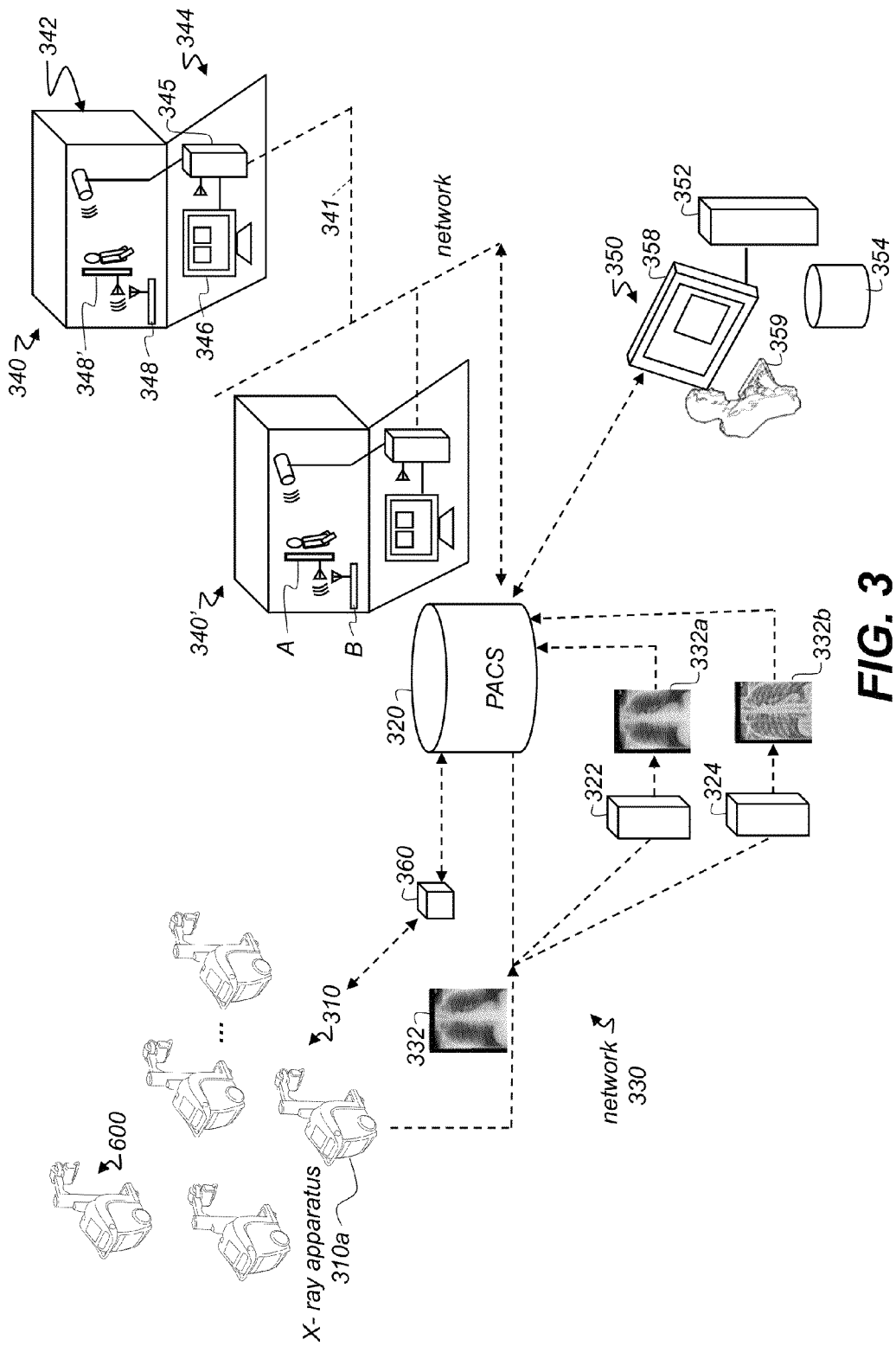
FIG. 3 is a schematic block diagram that shows a system for medical image procurement and management.

The schematic diagram of FIG. 3 shows an exemplary relationship of acquisition digital radiographic imaging apparatus (e.g., mobile DR imaging apparatus 310, x-ray imaging room 340), reviewing radiographic imaging apparatus (e.g., workstation 350) and/or storage radiographic imaging apparatus (e.g., PACS 320) and shows an overall relationship of a system to an embodiment of a prior image acquisition server 360. As noted previously, a primary image 332 that can be obtained from an image capture by a mobile DR imaging apparatus 310a. Primary image 332 can be directly provided for storage in the PACS 320 either as raw or pre-processed image data. Alternatively, the primary image 332 can be stored at the mobile DR imaging apparatus 310a and provided later to the PACS 320.

As shown in FIG. 3, an image management system 350 coupled to the system can include a logic processor 352, a memory 354, and an operator console that can include a display 358 and an operator entry device 359, such as a keyboard, mouse, touch screen, or other device for entry of operator commands. Commands at image management system 350 provide an additional capability for retrieval, review and/or management of the images stored in the system (e.g., PACS).

Still referring to FIG. 3, also connected to PACS 320 can be one or more X-ray imaging room 340 that can include an imaging room 342 (e.g., a shielded area in which a patient is imaged and containing an x-ray source), and a control room 344 that can include a display 346 and controller 345 for communicating with DR detectors 348 over a wireless interface and containing control logic for supporting and executing imaging operations with a selected DR detector 348'. In the embodiment shown, display 346 can be a touchscreen display, enabling the operator or technologist to easily control the X-ray imaging room 340 and select among DR detectors 348, 348' as an active DR detector 348' for obtaining the image using a graphical user interface (GUI). Imaging rooms 340 can be connected to the PACS 320 using a network 341 (e.g., wired, wireless, proprietary, public). Further, a communication network 330 can interconnect the PACS 320 with the mobile DR imaging apparatus 310 (directly or via the prior image acquisition server 360), the prior image acquisition server 360, the x-ray imaging room 340 and/or the image management system 350. The communication network 330 may be wired, wireless, proprietary, or public and comprised of many interconnected computer systems and communication links. Communication links may be hardwire links, optical links, satellite or other wireless communication links, wave propagation links, or any other mechanisms for communication of information.

Primary image 332 can be provided to one or more logic processors 322, 324 that each can perform some type of image processing and analysis operation before the primary images 332a and 332b can be stored in the PACS 320 along with acquired primary image 332. As shown in FIG. 3 the primary image 332 can be pre-processed and suitable for storage/archival as it is provided from mobile DR imaging apparatus 310a. It should be noted that, in an alternate embodiment, primary image 332 may be provided as raw data, requiring some amount of processing prior to storage in PACS 320. Logic processors 322 and 324 can generate additional processed secondary images 332a and 332b from raw data or from pre-processed primary image 332, as shown in FIG. 3. In one embodiment, the additional processed secondary images 332a and 332b can be companion images.

In one embodiment, the mobile radiography apparatus 600 can be used as one of the plurality of portable DR imaging apparatus 310.

For medical diagnosis, subsequent medical x-ray images can be compared by technicians/doctors/medical personnel to prior medical x-ray images of the same patient. It is preferable that the x-ray images different in time be obtained under the same conditions (e.g., exposure parameters). However, when different equipment, technicians, or medical facilities take the plurality of x-ray images there can be significant differences in the obtained x-ray images.

According to embodiments of the application, prior images can be reviewed before the imaging technician executes a current examination. The technician can "select prior parameters" from a desirable prior image and have a mobile x-ray unit be automatically set to the same parameters as the indicated desirable prior image.

Since prior images can be 10 MBs, 20 MBs, 30 MBs or more of data, and 10, 20 or more than 50 prior images may be related to a current examination, the prior images can constitute a large quantity of data or network traffic to transmit the prior images to the portable DR imaging apparatus 310. Pre-fetching of the prior images can be used to reduce network traffic or to timely provide prior images to the portable DR imaging apparatus 310 for display of a selected prior image. Pre-fetching (e.g., obtaining in advance of their use or need) images can be stored at the portable DR imaging apparatus 310 prior to a technician taking the unit 310 on their "rounds" to capture new/further images. Beneficially, pre-fetching can allow the technician to download the prior images over the wired network (e.g., limited access but faster) compared to a download over the wireless network available throughout the medical facility. The parameters (e.g., kVp level setting) of the pre-fetched prior images can be used to capture the new images for a current exam. Alternatively, pre-fetched prior images can be stored on the prior image acquisition server 360.

Embodiments of the application can include features of a mobile radiographic unit directed to displaying prior images.

According to embodiments of the application, the first display 610 and/or the second display 610' can provide prior images capabilities/functionality to the mobile radiography apparatus 600 such as but not limited to: (i) loading priors (e.g., previously captured image(s)) for a mobile imaging x-ray system; (ii) loading priors wirelessly or when directly connected to a network or image storage system (e.g., PACS 320); storing priors as full images or as a sub-sampled image to reduce disk space.

According to embodiments of the application, the first display 610 and/or the second display 610' can provide prior image display" feature/GUI with capabilities/functionality such as but not limited to: (i) display of a prior image itself; (ii) determining the size of the lung field in the image or determining prior image orientation (e.g., landscape vs. portrait) and determining for the same whether the user wants/selects consistent detector location & orientation between images, or the user indicates the prior was inadequate and a change should be made; (iii) displaying exposure technique information; (iv) matching current exposure techniques with prior images; (v) displaying SID (Source to Image Distance); (vi) matching SID with prior images; (vii) displaying angle measurements such as but not limited to patient angle—supine, upright or some angle in-between, X-Ray tube angle, X-Ray tube angle to patient angle—usually 90 but not always; (viii) matching angle with prior angle; (ix) displaying grid information such as but not limited to: was a grid used, grid ratio, transverse vs. longitudinal, recommended SID/SID range for that grid; (x) matching grid/no-grid and grid type with the prior; (xi) showing the prior exposure index to indicate if too much or too little exposure was used in the prior image; (xii) consistent rendering between prior image and new one (e.g., see below); (xiii) image capturing device or detector for the prior image (e.g., manufacturer, model, device name, etc.). There are variations in the quality (e.g., ISO speed, sensitivity) of detectors (e.g., better detectors require less dose) and also variations in the method different manufacturers use to calculate Exposure Index. Thus, knowing the image capturing device can benefit the technician.

Figure 4A:
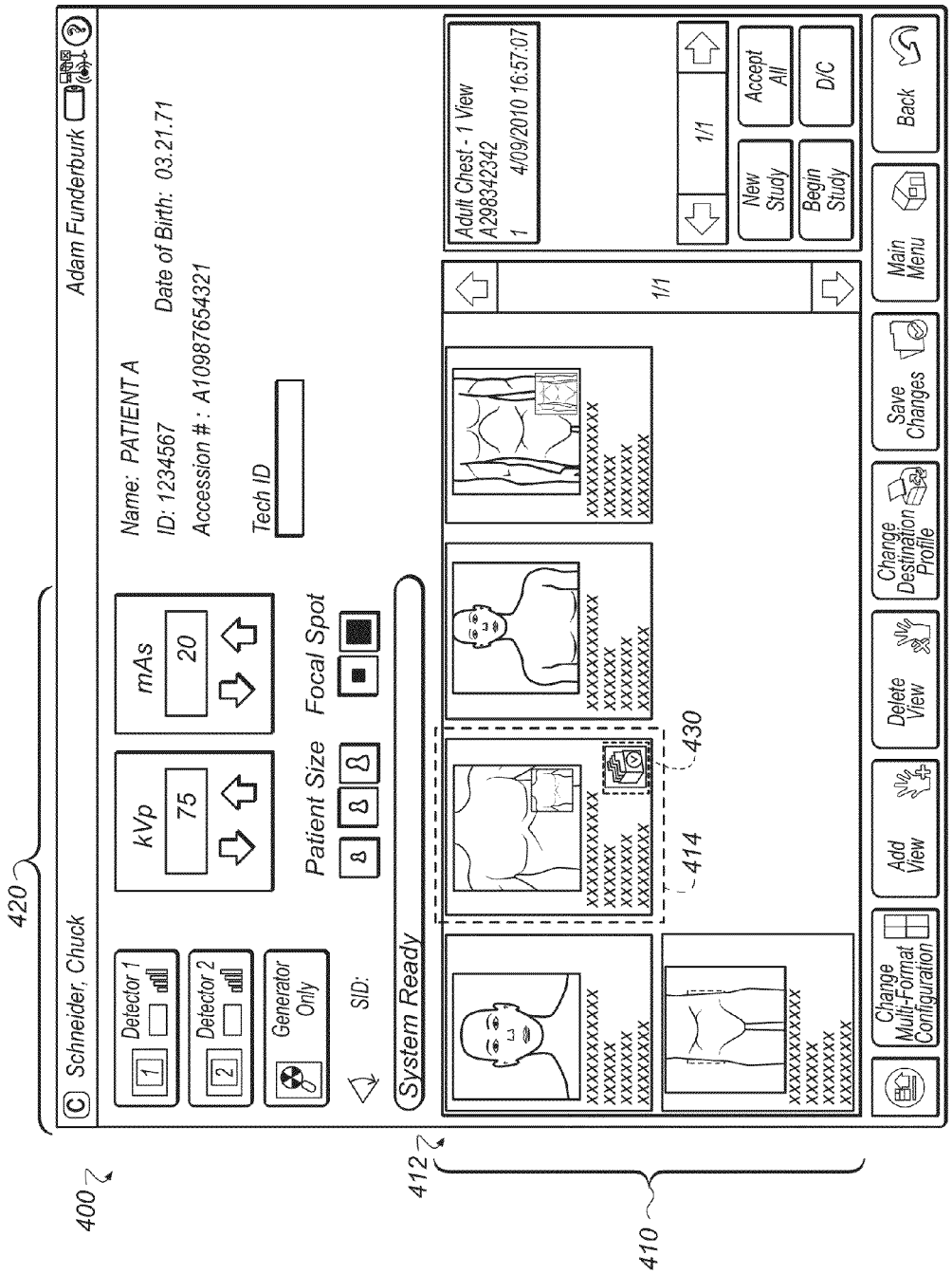
FIG. 4A is a diagram that shows an exemplary Image Acquisition Screen including an embodiment of a prior images capability according to the application.

FIG. 4A is a diagram that shows an exemplary image acquisition screen including an embodiment of a prior images capability according to the application. As shown in FIG. 4A, a series of images to be obtained for patient A are shown as a series of guidance images 410 for the series. A selected guidance image 412 can be highlighted and can generate the exposure information 420. As shown in FIG. 4A, a visual indication shown as an exemplary prior image button 430 can be provided on the guidance image (e.g., thumbnail). The prior image button 430 can be visible when the guidance image view is (i) configured to have priors and (ii) when one or more priors have been found (e.g., for that patient and that view). When the prior image button 430 can be selected (e.g., is displayed), prior image button 430 can preferably be active even when the guidance image with the prior image button 430 is not the currently selected guidance image. Thus, when priors are available, the operator can display the prior images by a single action (e.g., one button push). In one embodiment, the operator can hit the prior image button 430, and that guidance image becomes the currently selected guidance image and a prior image selection screen can be displayed.

FIG. 4B is a diagram that shows an exemplary prior image selection screen including an embodiment of a sorted prior images list according to the application. As shown in FIG. 4B, a prior image selection screen 440 can include a copy technique button 442, an ordered list 444 of available prior images, a prior thumbnail 446 displayed for a corresponding selected prior image 447 in the list 444, and a quality indication 448 for the corresponding selected prior image 447.

In one embodiment, the prior image selection screen 440 can be a modal dialogue within the display so that all other fields are dimmed and made inactive. Preferably, the prior image selection screen 440 can be dimensioned to allow the guidance images to be visible on the display at the same time. The prior image selection screen 440 can also include information (e.g., metadata) regarding the selected prior image 447 such as but not limited to a view name (e.g., displayed with a spatial relationship to the thumbnail image 446), date and time, kVp, mAs, SID/SOD, posture, or grid presence or absence (e.g., shown as "Grid" or "Non-Grid") and a close button.

In one embodiment, the quality indication 448 preferably can be a qualitative indication and a quantitative indication. For example, the quality indication 448 can be the exposure index. Alternatively, the quality indication 448 can be the Signal to Noise ratio calculation. However, the prior thumbnail 446 displayed can be displayed at a size and/or quality to provide the operator sufficient information to determine a quality of the prior image 447. The technician can view the prior thumbnail 446 image for proper positioning. Further, the technician can view a zoomed image 446' (e.g., FIG. 4C) of the prior thumbnail 446 image to look for noise.

In one embodiment, the copy technique button 442, when selected, can copy the generator settings used in the displayed prior 447 to the current guidance image's 414 settings. Selection of the copy technique button 442 can close the prior image selection screen 440.

The ordered list 444 of available prior images for the body part can be visually divided (e.g., to the right, left, above) from the thumbnail 446. In one embodiment, the prior images can be associated with the anatomy of the guidance image and not the specific view itself in the guidance image. Thus, previous images of the same body part can be considered priors regardless of their view (e.g., a "Chest—PA—Erect" image can be considered a prior image for a "Chest—AP—Supine" in the current procedure). The ordered list 444 of prior images can be labeled with the view name and date/time of the image and sorted by characteristics such as (a) reverse-chronological order (e.g., starting with most recent), (b) specific view for body part, (c) DICOM header information, (d) use the HIS/RIS Procedure Code to determine what images were done for the same procedure (e.g., for variations in body part naming between vendors). (e) use SNOMED codes (Systematized Nomenclature of Medicine—Clinical Terms) to identify body part and projection in a vendor neutral way. There can be a visual indication (e.g., such as a highlighted border) of which prior image in the list is currently displayed as a thumbnail. Multiple pages of available priors can exist and various methods (e.g., vertical scrollbar) can be used to browse the multi-page list. Alternatively, the prior images 444 can be associated with the specific view itself in the guidance image.

Figure 4C:
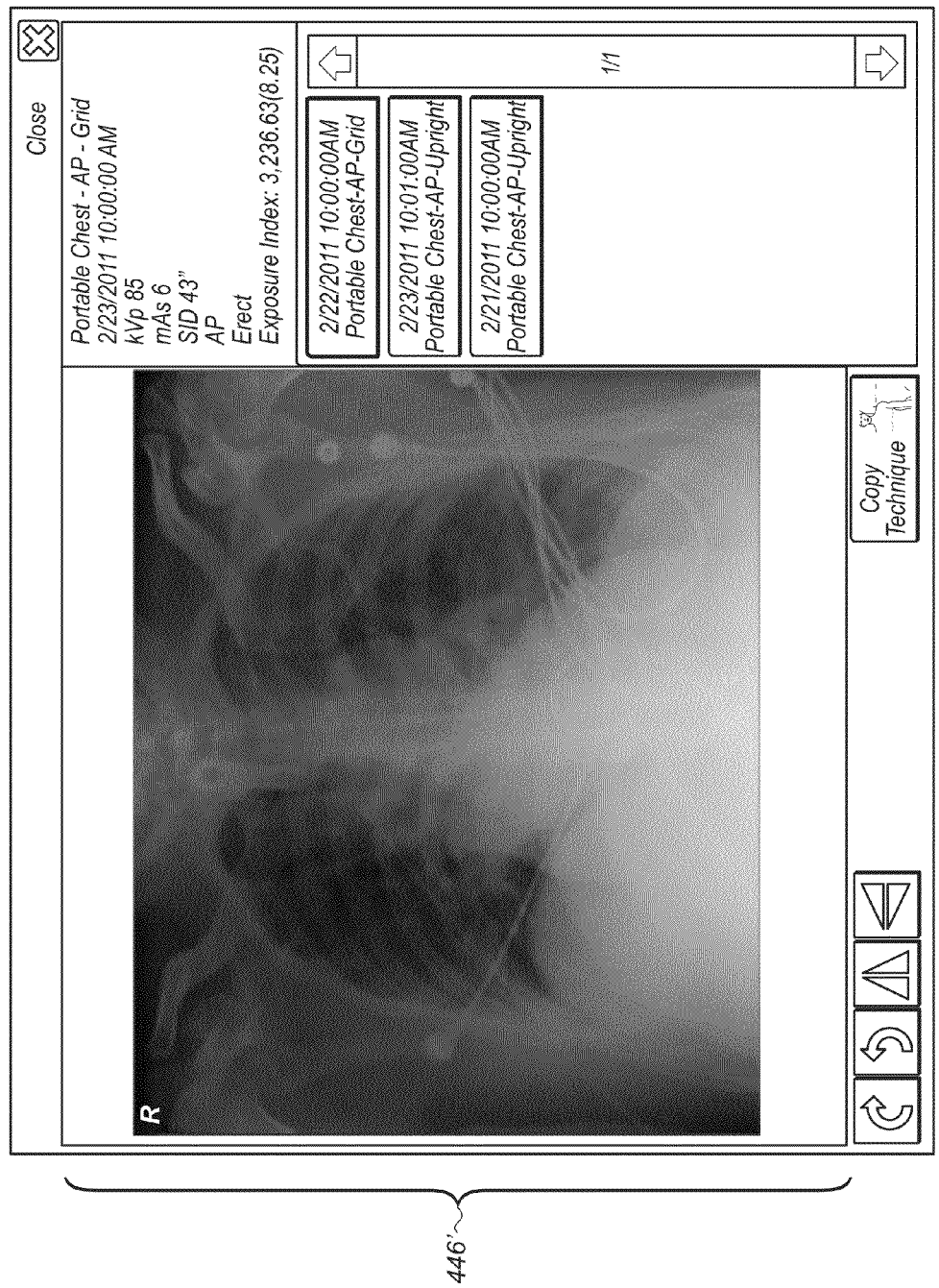
FIG. 4C is a diagram that shows an exemplary higher resolution selected prior image screen according to the application.

FIG. 4C is a diagram that shows an exemplary higher resolution selected prior image screen according to the application. In one embodiment, the thumbnail image 446 can be interactive so that selection of the prior image 447 can display a larger-resolution view of the current thumbnail image 446' (e.g., as another closable modal dialogue screen). Thus, selection of the prior image 447 as shown in FIG. 4B can display a higher resolution selected prior image screen 460 that can include a representation 446' including a higher resolution representation (e.g., relative to the thumbnail image 446) of the selected prior image 447. For example, the higher resolution prior image 446' can have the same aspect ratio as the thumbnail image 446, but use 100%, 80%, 60%, 40% or a specific number of pixels (e.g., 600 by 480) of the display screen. The higher resolution selected prior image screen 460 can include the copy technique button 442 and the displayed information (e.g., same layout) as the prior image selection screen 440. FIG. 4C can be an exemplary higher resolution selected prior image screen for display at the first display 610 or the second display 610'.

Figure 4D:
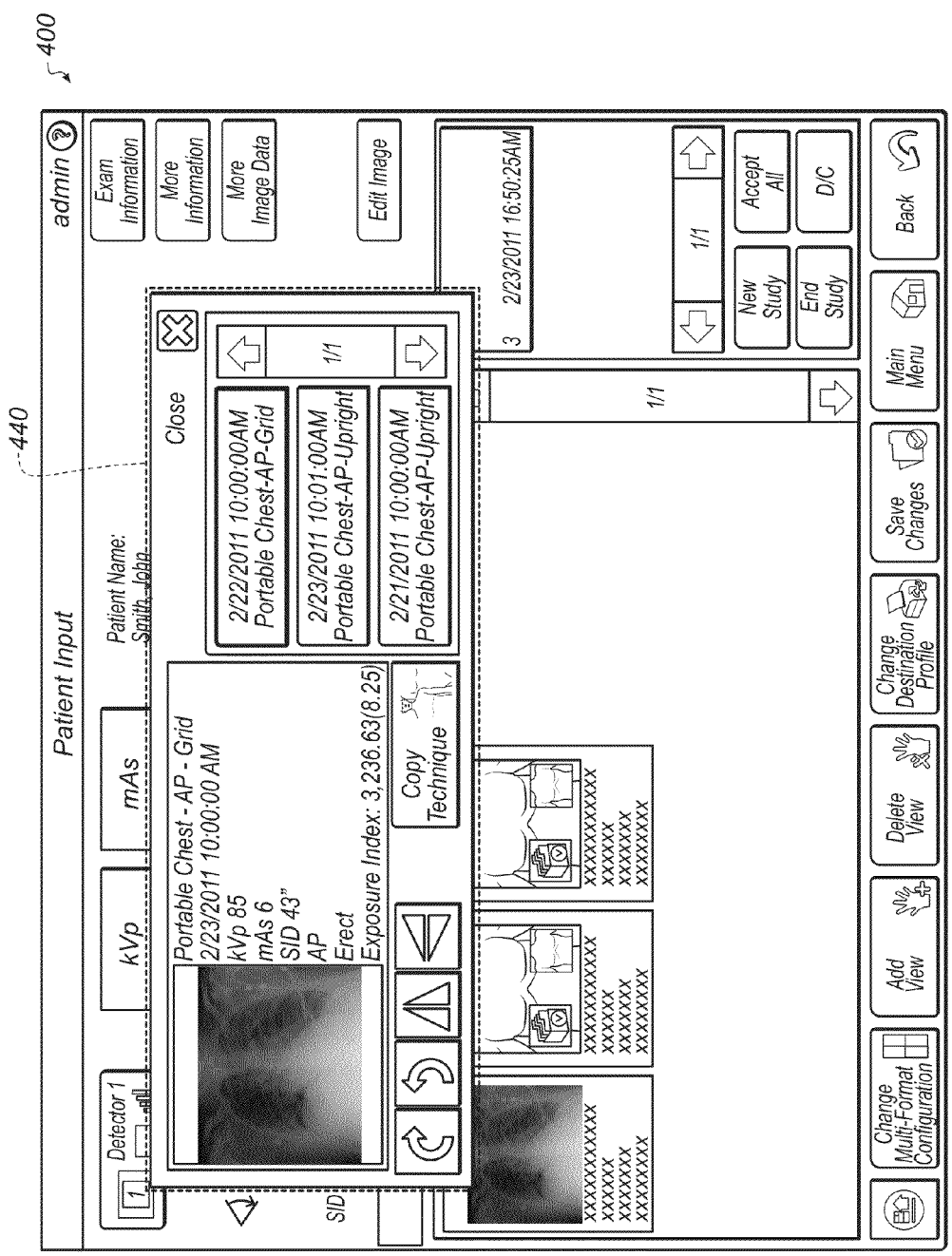
FIG. 4D is a diagram that shows an exemplary prior image selection screen displayed as an active screen with an inactive image acquisition screen according to the application.

FIG. 4D is a diagram that shows an exemplary prior image selection screen displayed with an image acquisition screen according to the application. As shown in FIG. 4D, the prior image selection screen 440 can be displayed as an active screen with the image acquisition screen 400 inactive (e.g., displayed grey underneath).

In one embodiment, the prior image can be obtained from comes from an imaging system (e.g., different manufacturer or an in-room radiographic system) that can include differing generators or x-ray sources. As all generators are different, for selected priors, the mobile radiography system 600 can not achieve the same technique. When the technician selects to Copy Techniques 442, the mobile radiography system 600 may need to convert the selected techniques into a corresponding technique the system 600 can perform or provide. For example, when the Prior image (for the Copy Technique 442) was for a 3 point technique specifying 100 kVp 100 mA for 1 second and the system 600 can only do 2 point techniques, where the user specifies kVp & mAs; the prior image mAs=100 mA*b second=100 mAs and the system 600 can use a 200 mA*0.5 second exposure to achieve a 100 mAs. Preferably, when the copy techniques 442 operation requires a technique conversion, a confirmation modal dialog can be provided to the technician for acknowledgement and acceptance of the corresponding technique (e.g., instead of the copied technique). Preferably, the confirmation modal dialog provides the desired exposure settings (e.g., kVp & mAs) and the modified copied exposure settings (e.g., kVp & mAs) to the technician for single action acceptance.

In one embodiment, the visual indication of the image quality or quality indication shown in FIG. 4B comprises a relationship to a prescribed amount of radiation dose or a relationship to an image-to-noise characteristic, wherein the visual indication of image quality comprises a first quantitative value (e.g., exposure index, quality indication 448) and a second qualitative value for the first quantitative value (e.g., optional rating 449 (a range from 0 (bad) to 1 (excellent)); color coded icon (red—unacceptable, yellow—acceptable but poor, green—good quality); a number of standard deviations away from a desired first quantitative value).

To perform prior images selection for review, display or to copy techniques, embodiments according to the application can have a requirement to consistent render images (e.g., x-ray images) from different x-ray sources, image processing, imaging apparatus, imaging standards and languages. Thus, consistent rendering of priors can be an extensive and difficult task.

According to embodiments of the application, consistent rendering can include obtaining information about and analyzing the prior image so that various priors can be compared and a new image can be processed in a similar fashion. For images acquired on a first type of imaging systems (e.g., imaging systems developed by Carestream Health), the prior image analysis and selection of desirable or needed information can be performed at image processing time, which can be included or stored with the prior image (e.g., include information in the DICOM header of the prior image). For the first type of imaging system, an imaging system reviewing priors for display or selection need not perform any image analysis on the prior. The system can obtain the necessary and/or data can be obtained from the DICOM header or the retrieved image.

For a second type of imaging system (e.g., related art imaging system), information used to be consistently render or to be displayed with priors may not be in the DICOM header of the prior image. In this situation, after being loaded, the mobile radiography apparatus 600 can analyze the prior image to determine image processing parameters required for consistent rendering. This analysis can be done on the mobile x-ray cart or at the prior image server 360, which can forward the information (e.g., for consistent rendering) to the mobile radiography apparatus 310, 600.

Prior Image Server

The system can include a Prior Image Server. This is a server that fetches the prior images from the PACS (Picture Archive and Communication System, such as available from Carestream Health, Inc.) so that the mobile X-Ray units don't need to access the PACS directly. For example, there is concern over the network traffic (e.g., wireless communications) related to the size of the prior images, the number of the prior images related to a current examination, the number of the examinations on a worklist for a mobile x-ray cart, and the number of mobile x-ray carts to request priors in one day (e.g., receiving worklists). Medical diagnostic images (e.g., x-ray priors) can be 5M, 10M, 25M, 40M or more per image. According to the application, there are several method embodiments of prior image server operations to provide a prior image server processor and/or capability. Embodiments of a prior image server can for example, pre-fetch all potential priors, pre-fetch on an actionable list (e.g., To Do List, Worklist) or fetch potential priors on-demand. In one embodiment, a prior image server can access priors over a wired network (e.g., HIS/PACS), sub-samples (e.g., 8-bit) and then distribute reduced size prior images to reduce PACS load and wired/wireless network load.

Prior Image Server Methods

Referring to FIG. 5, a flow chart that shows an embodiment of a first method of operating prior image acquisition according to the application will now be described. As shown in FIG. 5, a method 500 for operating prior image acquisition will be described using and can be implemented by embodiments of apparatus shown in FIG. 3; however, the method of FIG. 5 is not intended to be limited thereby.

As shown in FIG. 5, a prior image acquisition server 360 can access a combined worklist/examination procedures for all/plurality of mobile units 310 (e.g., for a medical facility) (operation block 510). Priors that can be used for any of the accessed examination procedures can be determined (operation block 520). The determined priors can be fetched (e.g., from PACS 320) before the exams are performed. For example, the fetched priors can be stored at the prior image acquisition server 360 (operation block 530). As shown in FIG. 5, in one embodiment, the fetched priors can be modified to reduce the associated amount of data and network traffic to receive the fetched priors at corresponding mobile units 310. Thus, the fetched priors can be sub-sampled (operation block 540), which can make distribution to the mobile units 310 faster. Further, any unnecessary image information (e.g., DICOM information) can be reduced or removed (operation block 550) to make distribution faster. Accordingly, the fetched priors can be optionally modified as prescribed (operation blocks 540, 550) before the corresponding one or more mobile unit(s) 310 receive the priors (operation block 560). In one embodiment, the mobile unit(s) 310 can access and retrieve priors (e.g., from the prior image acquisition server 360) as needed. In one embodiment, the mobile unit(s) 310 can receive priors (e.g., from the prior image acquisition server 360) transmitted thereto. In one embodiment, the mobile unit(s) 310 can retrieve or receive priors on demand. As shown in FIG. 5, in one embodiment, the mobile units 310 have wireless access to the fetched priors at the prior image acquisition server 360 throughout (e.g., continuously) the medical facility rounds.

In one embodiment, a prescribed number of priors can be used. Thus, a set number of three priors or five priors can be pre-fetched for each image to be taken. Preferably, the prescribed number can be user configurable within a range (e.g., 1-12) by a user or selected within the range by examination type.

In a second embodiment of a method for operating prior image acquisition, the mobile units 310 do not have access to the prior image acquisition server 360 as needed or at all after a (e.g., wired) connection at the start of the rounds/worklist. In this embodiment, selected priors can be pushed to any mobile unit(s) 310 that might perform the exam before the exam is started (e.g., over a wired or wireless network). Even in a wired network, reducing load on the PACS server by fetching each prior only once can improve performance and the mobile units 310 can also receive modified priors or the sub-sampled priors.

In a third embodiment of a method for operating prior image acquisition (otherwise similar to the first and second embodiments), the mobile units 310 would receive or a system can distribute the full DICOM images as priors.

In a fourth embodiment of a method for operating prior image acquisition, priors are delivered directly to the prior image acquisition server 360. During medical facility operations, some exams are ordered and performed quickly. The prior image acquisition server 360 might not have time to fetch corresponding priors in these circumstances. The fourth embodiment of a method for operating prior image acquisition can deliver the prior images directly to the prior image acquisition server 360 (e.g., either by an x-ray cart or the PACS can forward the images). Then the prior image acquisition server 360 would already have any desired priors stored (e.g., on the hard drive, RAM, ROM). Periodically, repeatedly, or after a set time of a few days, the priors would be automatically cleaned up at the prior image acquisition server 360.

In one embodiment, the prior image acquisition server 360 can ask a medical facility information service (e.g., Hospital Information Systems/Radiology Information System HIS/RIS) for a list of exams based on selected filters (e.g., Station Name, AE Title, Date/Time range, Modality (CR, DR, Mammography), etc.). The medical facility information service can respond with a list of exams. The prior image acquisition server 360 can request a medical image archive (e.g., the PACS) for a list of images that match the patient ID (e.g., or Name, Date of Birth, identifier) of the new exams from the HIS/RIS. The prior image acquisition server 360 can further filter the request by Modality, Date/Time, Body Part, Procedure Code or the like. The Date/Time filtering can be short (e.g., past week for a mobile cart) or long (last year's images for a mammography system). After receipt of the list of available prior images (e.g., based on the filters) from the PACS, the prior image acquisition server 360 can decide what selected/specific images of the available images to request from the PACS, which can send back just those specific images. Once the prior image acquisition server 360 has the selected prior images, it can be determined (e.g., as described herein) which are the most relevant and/or sort the selected prior images. The prior image acquisition server 360 can also include any images that were acquired by and remain at the one or more mobile radiography apparatus 310, 600, and can include or add such local priors into the prior image list for sorting/relevance prioritization.

Figure 6B:
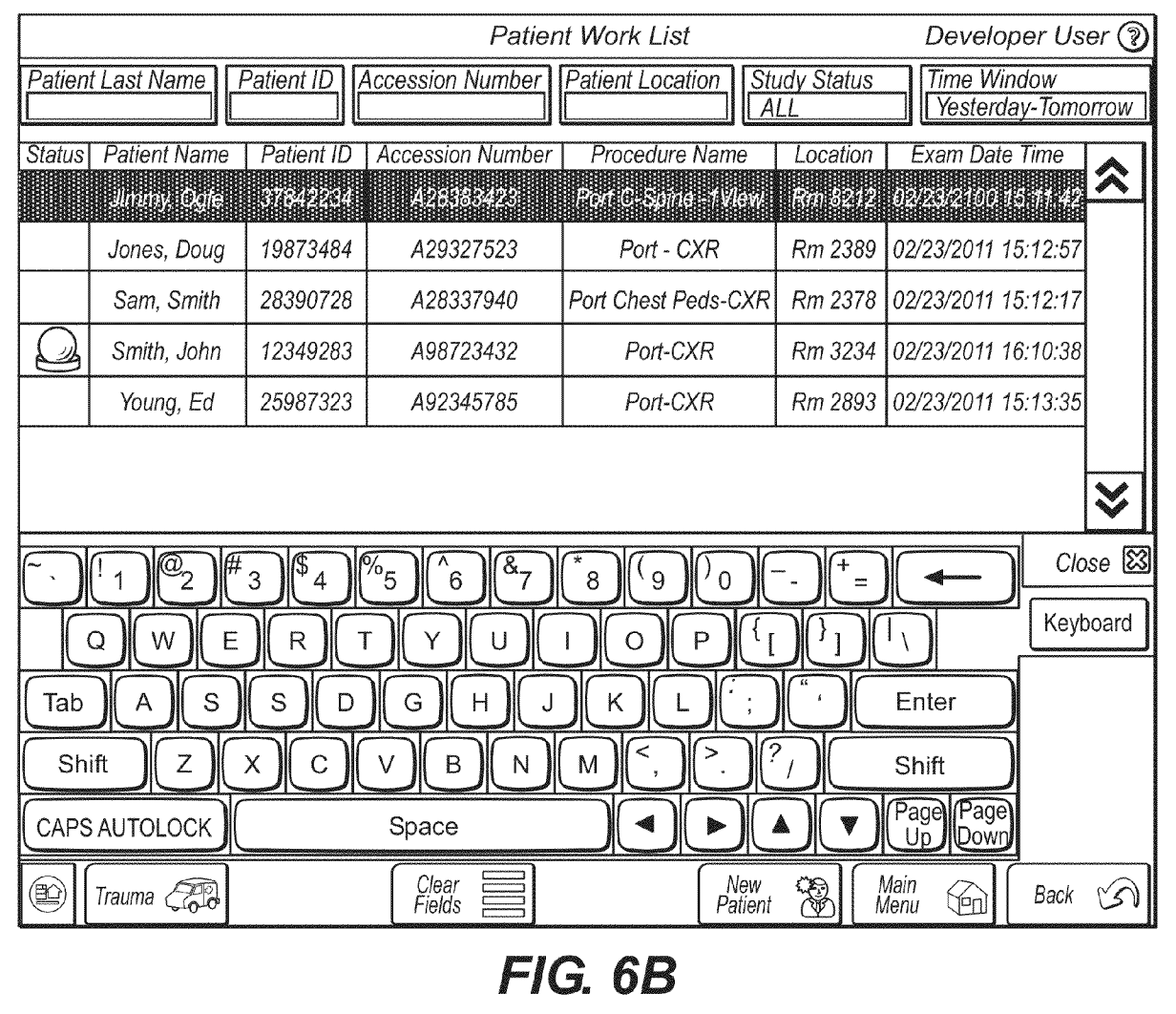
Figure 8:
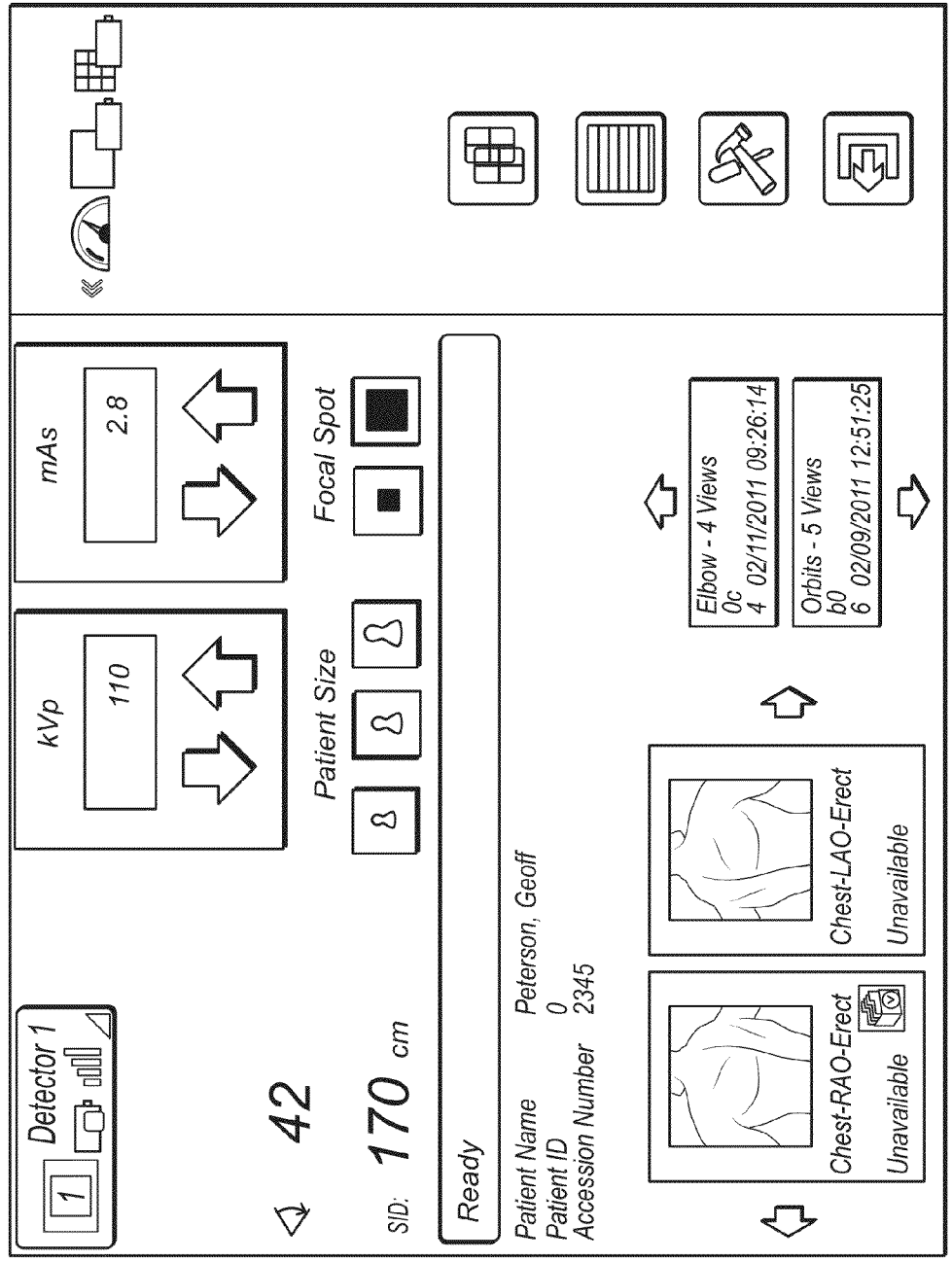
Figure 9:
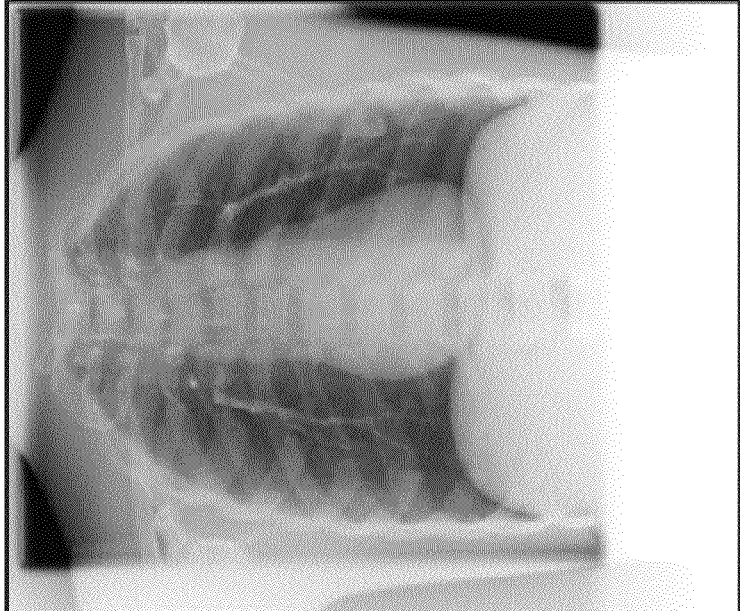

FIGS. 6A-9 are diagrams that illustrate exemplary non-limiting representative functions illustrated on an embodiment of a display of a mobile x-ray imaging apparatus according to the application. As shown in FIG. 6A, an example of a work list is shown on a monitor of the second display 610'. As shown in FIG. 6B, an example of a work list is shown on a monitor of the first display 610. As shown in FIG. 7, an example of a new examination/procedure information/requirement for that technician and/or patient is shown on a display of a mobile x-ray imaging apparatus. As shown in FIG. 8, an example of generator controls is shown on a display of a mobile x-ray imaging apparatus. As shown in FIG. 9, an example of newly acquired image and patient information is shown on a monitor of the second display 610'.

FIG. 10 is a diagram that shows an exemplary embodiment of a display/monitor as a second display mounted to a boom assembly of a mobile radiography unit according to the application. As shown in FIG. 10, the second display 610' can be mounted to a collimator 1045 of an x-ray source 1040 of a boom assembly of a mobile radiography unit. "Boom assembly" can refer to the x-ray tube, a housing for the x-ray tube, a collimator, a structure/box below the collimator used to achieve (for example, 30 cm) separation between the tube and the patient, or any portion of the adjustable support column that can be used to position the tube over the patient. In one embodiment, the collimator 1045 is rotably mounted to the x-ray source 1040 so that the collimator 1045 (e.g., second display 610') can swivel at least 90 degrees, at least 180 degrees or 360 degrees. As shown in FIG. 10, the second display 610' is coupled to a plurality of handles for ease of positioning. Alternatively, the second display 610' can be mounted to (e.g., rotatably) an x-ray source 1040 above a collimator 1045 of a boom assembly of a mobile radiography unit.

As described in selected embodiments, information related to prior images can be displayed side-by-side with similar configured information for a current exam. For example, information can be displayed side-by-side with similar "live" information. Accordingly, the prior SID vs. the current distance from the x-ray tube to the detector can be displayed. Further, prior image information can be used to automatically change the configured view information for the current exam. For example, adjust kVp for this current exam to match the kVp used in a prior exam. In one embodiment, the second display 610' and/or the first display 610 can be actuated for example using an attached keyboard/mouse, a remote control, a touch screen, a tethered, control, an operable screen or the like.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Embodiments of the prior image server 360 can pre-fetch priors for every new study as soon as it is created by the HIS/RIS Service, fetch on demand (e.g., when the technician opens the study), fetch priors for a study after the user has indicated that they intend to perform that study (e.g., to do list). In one embodiment, the prior image server 360 can wait for the apparatus 310/technician to tell indicate what studies will be performed, and then send the priors to the apparatus 310 before the exam is started. The apparatus 310 can indicate which exams are intended to perform by opening an exam, by barcode scanning a requisition form, or building a to do list.

Embodiments according to the application can provide various advantages including a "Prior Image Display" feature that can assist technicians (e.g., users) by providing information about the patients last exam and/or plurality of previous exams (e.g. subset or all) including positioning, technical information and patient specific anatomy characteristics. Embodiments of a Prior Image Display can be achieved by requesting the patients last exams image(s) from the PACS and having the images available for review. In one embodiment, data from the DICOM header can be extracted.

In one embodiment, the second display 610' and/or the first display 610 can be actuated for example using an attached keyboard/mouse, a remote control, a touch screen, a tethered control, an operable screen or the like. In one embodiment, the first display 610 can implement a subset of the functionality of the second display 610'. In another embodiment, the second display 610' can implement a subset of the functionality of the first display 610. Alternatively, information and controls capable of use at the first display 610 can be provided (e.g., identically) at the second display 610'.

As will be appreciated by one skilled in the art, the present invention may be embodied as a system, method, or computer program product. Accordingly, an embodiment of the present invention may be in the form of an entirely hardware embodiment, an entirely software embodiment (including firmware, resident software, micro-code, and other suitable encodings) or an embodiment combining software and hardware aspects that may all generally be referred to herein as a "circuit" or "system." Furthermore, the present invention may take the form of a computer program product embodied in a computer-readable storage medium, with instructions executed by one or more computers or host processors. This medium may comprise, for example: magnetic storage media such as a magnetic disk (such as a hard drive or a floppy disk) or magnetic tape; optical storage media such as an optical disc, optical tape, or machine readable bar code; solid state electronic storage devices such as solid state hard drives, random access memory (RAM), or read only memory (ROM); or any other physical device or medium employed to store a computer program. The computer program for performing the method of the present invention may also be stored on computer readable storage medium that is connected to a host processor by way of the internet or other communication medium.

Those skilled in the art will readily recognize that the equivalent of such a computer program product may also be constructed in hardware. The computer-usable or computer-readable medium could even be paper or another suitable medium upon which executable instructions are printed, as the instructions can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport computer instructions for use by, or in connection with, an instruction execution system, apparatus, or device.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A mobile x-ray radiography apparatus comprising:
   a moveable transport frame;
   adjustable supporting means for moving three-dimensionally, where the adjustable supporting means is coupled to the movable transport frame; and
   x-ray generating means mounted to the adjustable supporting means; and
   graphic user interfacing means for controllably displaying an icon being a related prior image, the icon viewable in a portion of said graphic user interfacing means that identifies an exposure performed by the x-ray generating means; and
   display means for displaying at least the graphic user interfacing means.

2. The mobile x-ray radiography apparatus of claim 1, comprising storing means for storing computer-readable instructions identifying among a plurality of related prior images, where the storing means stores at least two x-ray image acquisition parameters for each of the related prior images.

3. The mobile x-ray radiography apparatus of claim 2, further comprising copying means for copying said at least two x-ray image acquisition parameters from a first GUI displaying one related prior image to a different GUI.

4. A mobile radiographic imaging apparatus for radiographically imaging a patient, the apparatus comprising:
   a moveable transport frame;
   an adjustable support structure connected to the movable transport frame; and
   an x-ray source mounted to the adjustable support structure, the adjustable support structure configured to allow the x-ray source to be manually positioned;
   a display comprising a selection screen, wherein the apparatus is configured to determine that a related prior radiographic digital image of the patient is available to be accessed by the apparatus, and wherein the apparatus is configured to generate a visible indicator on the display when the prior radiographic digital image is determined to be available, in response to a request input by an operator on the selection screen; and
   storage, in which the apparatus is configured to store the related prior radiographic digital image,
   wherein the apparatus is configured to store exposure parameter data in the storage in association with the related prior radiographic digital image, the exposure parameter data including an intensity level of x-ray radiation used to capture the related prior radiographic digital image, and wherein the selection screen includes means for the operator to select the exposure parameter data associated with the related prior radiographic digital image to be automatically applied by the mobile radiographic imaging apparatus to a current exposure.

5. The mobile radiographic imaging apparatus of claim 4, wherein the apparatus is configured to generate on the selection screen a thumbnail image of the related prior radiographic digital image.

6. The mobile radiographic imaging apparatus of claim 5, wherein the apparatus is configured to generate on the selection screen a visible indicator to indicate a level of quality of the related prior radiographic digital image corresponding to the thumbnail image.

7. The mobile radiographic imaging apparatus of claim 4, wherein the apparatus is configured to determine that the available related prior radiographic digital image comprises a digital image captured via an exposure previously performed by the x-ray source based on data stored in the storage in association with the related prior radiographic digital image.

8. The mobile radiographic imaging apparatus of claim 4, wherein the selection screen includes means for receiving the request input by the operator.

9. The mobile radiographic imaging apparatus of claim 4, wherein the apparatus further comprises a network connection configured to access a network connected image archive for retrieving therefrom the related prior radiographic digital image before storing it in the storage and displaying it on the display.

10. A mobile x-ray radiography apparatus for digitally imaging a patient, the apparatus comprising:
a moveable transport frame;
an adjustable support structure coupled to the movable transport frame;
an x-ray source mounted to the adjustable support structure;
a display;
means for determining that at least one stored prior digital image is related to a currently scheduled radiographic examination and is accessible by the apparatus; and
means for generating a graphical user interface (GUI) on the display, for generating a visual indication on the GUI when the at least one stored prior digital image is determined to be related to the currently scheduled radiographic examination and is accessible by the apparatus, and for presenting on the display the stored prior digital image in response to a selection input by an operator.

11. The mobile x-ray radiography apparatus of claim 10, further comprising network interconnection means for accessing a digital database storing the at least one related prior digital image.

12. The mobile x-ray radiography apparatus of claim 11, wherein the means for generating is configured to display a plurality of related prior digital images on the display in order of a relevance value of each digital image, wherein the apparatus further comprises means for determining the relevance value of each digital image based on a capture time closest in time to a present time, for determining a proprietary view name for each digital image, for determining a body part name for each digital image, for determining a procedure code for each digital image, and for determining a patient identifier for each digital image, or a combination thereof.

13. The mobile x-ray radiography apparatus of claim 11, wherein the means for generating is configured to present on the display a visual indication of image quality of a related prior digital image selected by the operator.

14. The mobile x-ray radiography apparatus of claim 13, wherein the means for generating is configured to present on the display a sub-sampled image of the related prior digital image selected by the operator.

15. The mobile x-ray radiography apparatus of claim 13, wherein the visual indication of the image quality comprises a color coded indicator, a numerical value, or a combination thereof.

16. The mobile x-ray radiography apparatus of claim 15, wherein the visual indication of image quality is based on a radiation level, an image-to-noise level, or a combination thereof, of the related prior digital image selected by the operator.

17. The mobile x-ray radiography apparatus of claim 11, wherein the apparatus is configured to pre-fetch the at least one related prior digital image before the currently scheduled radiographic examination is performed by the apparatus.

18. The mobile x-ray radiography apparatus of claim 17, further comprising digital storage, and means for storing in the digital storage exposure parameters in association with the at least one related prior digital image, and wherein the apparatus is configured to automatically access the exposure parameters and apply the accessed exposure parameters for the currently scheduled radiographic examination to be performed by the apparatus in response to a request input by the operator.

* * * * *